US012600922B2

(12) United States Patent
Lundberg et al.

(10) Patent No.: US 12,600,922 B2
(45) Date of Patent: Apr. 14, 2026

(54) REDUCING AGENT AS CORROSION INHIBITOR FOR MACHINE WAREWASH

(71) Applicant: ECOLAB USA INC., Saint Paul, MN (US)

(72) Inventors: Steven Lundberg, Saint Paul, MN (US); Andrew M. Jensen, Saint Paul, MN (US); John Mansergh, Saint Paul, MN (US); Carter M. Silvernail, Saint Paul, MN (US); Erik C. Olson, Saint Paul, MN (US); Derrick Anderson, Saint Paul, MN (US); Mara Carver, Saint Paul, MN (US)

(73) Assignee: ECOLAB USA INC., Saint Paul, MN (US)

(*) Notice: Subject to any disclaimer, the term of this patent is extended or adjusted under 35 U.S.C. 154(b) by 175 days.

(21) Appl. No.: 17/452,882

(22) Filed: Oct. 29, 2021

(65) Prior Publication Data

US 2022/0135907 A1 May 5, 2022

Related U.S. Application Data

(60) Provisional application No. 63/107,513, filed on Oct. 30, 2020, provisional application No. 63/260,237, filed on Aug. 13, 2021.

(51) Int. Cl.
*C11D 3/00* (2006.01)
*A61L 2/18* (2006.01)
(Continued)

(52) U.S. Cl.
CPC .............. *C11D 3/0073* (2013.01); *A61L 2/18* (2013.01); *C11D 3/044* (2013.01); *C11D 3/046* (2013.01);
(Continued)

(58) Field of Classification Search
None
See application file for complete search history.

(56) References Cited

U.S. PATENT DOCUMENTS 3,741,901 A 6/1973 Ziffer
4,268,406 A 5/1981 O'Brien et al.
(Continued)

FOREIGN PATENT DOCUMENTS

EP 0034393 A1 8/1981
EP 0234675 A2 * 2/1987 ............ A47L 15/00
(Continued)

OTHER PUBLICATIONS

International Search Report and Written Opinion in PCT/US2021/057336, mailed Feb. 8, 2022, 14 pages.
(Continued)

*Primary Examiner* — Kaj K Olsen
*Assistant Examiner* — Arlyn I Rivera-Cordero
(74) *Attorney, Agent, or Firm* — McKee, Voorhees & Sease, PLC

(57) ABSTRACT

Warewash detergent compositions with reducing agents to overcome corrosion challenges in stainless steel dish machines subject to conditions from chlorine sanitizing rinse steps (or other oxidizing chlorine containing compositions) are provided. Liquid and solid detergent composition beneficially containing a reducing agent that reacts with chlorine introduced in sanitizing rinse steps that follow detergent cleaning steps are provided. Methods for ware washing using the detergent compositions with reducing agents and methods for reducing residual chlorine in a ware washing cycle are also provided.

8 Claims, 4 Drawing Sheets

(51) Int. Cl.
*A61L 101/06* (2006.01)
*C11D 3/04* (2006.01)
*C11D 3/33* (2006.01)
*C11D 3/36* (2006.01)
*C11D 3/37* (2006.01)

(52) U.S. Cl.
CPC ................ *C11D 3/33* (2013.01); *C11D 3/365* (2013.01); *C11D 3/3757* (2013.01); *A61L 2101/06* (2020.08); *A61L 2202/17* (2013.01); *C11D 2111/14* (2024.01)

(56) References Cited

U.S. PATENT DOCUMENTS

| | | | | |
|---|---|---|---|---|
| 4,421,664 | A | 12/1983 | Anderson | |
| 5,336,430 | A * | 8/1994 | Bahary | C11D 3/0042 510/222 |
| 5,691,292 | A | 11/1997 | Marshall et al. | |
| 5,710,115 | A * | 1/1998 | Patel | C11D 3/3945 510/226 |
| 5,837,663 | A | 11/1998 | Nicholson et al. | |
| 6,368,420 | B1 | 4/2002 | Angevaare et al. | |
| 6,921,743 | B2 | 7/2005 | Scheper et al. | |
| 7,153,820 | B2 | 12/2006 | Olson et al. | |
| 7,625,533 | B2 | 12/2009 | Doona et al. | |
| 7,759,299 | B2 | 7/2010 | Smith et al. | |
| 7,892,536 | B2 | 2/2011 | Kelemen et al. | |
| 8,343,328 | B2 | 1/2013 | Hook et al. | |
| 8,636,919 | B1 | 1/2014 | Hughes | |
| 9,254,400 | B2 | 2/2016 | Hilgren et al. | |
| 9,517,934 | B2 | 12/2016 | Doona et al. | |
| 9,879,206 | B2 | 1/2018 | Rischmiller et al. | |
| 10,059,910 | B2 | 8/2018 | Peters et al. | |
| 10,179,892 | B2 | 1/2019 | Chan et al. | |
| 10,316,272 | B2 | 6/2019 | Dotzauer et al. | |
| 10,767,140 | B2 | 9/2020 | Watson | |
| 2005/0075257 | A1 | 4/2005 | Scheper et al. | |
| 2013/0172228 | A1 | 7/2013 | Bartelme et al. | |
| 2014/0251385 | A1 | 9/2014 | Kelly-Murray et al. | |
| 2019/0071619 | A1 | 3/2019 | Malten et al. | |
| 2019/0376008 | A1 | 12/2019 | Liu et al. | |
| 2020/0056122 | A1 | 2/2020 | Vind et al. | |
| 2020/0157475 | A1 * | 5/2020 | Piorkowski | C11D 1/22 |

FOREIGN PATENT DOCUMENTS

| | | | |
|---|---|---|---|
| EP | 0723006 | A2 | 7/1996 |
| EP | 1789526 | A1 | 5/2007 |
| EP | 2617804 | A1 | 7/2013 |
| SU | 479804 | A1 | 8/1975 |

OTHER PUBLICATIONS

International Searching Authority in connection with PCT/US2021/057336 filed Oct. 29, 2021, "The International Search Report and the Written Opinion of the International Searching Authority, or the Declaration", 16 pages, mailed Feb. 8, 2022.

* cited by examiner

100 Cycle, 16gpg, 2000ppm Detergent

REDUCING AGENT AS CORROSION INHIBITOR FOR MACHINE WAREWASH

CROSS-REFERENCE TO RELATED APPLICATIONS

This application claims priority under 35 U.S.C. § 119 to U.S. Provisional Application Ser. No. 63/107,513, filed Oct. 30, 2020, and U.S. Provisional Application Ser. No. 63/260,237, filed Aug. 13, 2021, both titled "Reducing Agent as Corrosion Inhibitor for Machine Warewash" and each of which are herein incorporated by reference in its entirety including without limitation, the specification, claims, and abstract as well as any figures, tables, or examples thereof.

FIELD OF THE INVENTION

The invention relates to warewash detergent compositions with reducing agents to overcome corrosion challenges in stainless steel dish machines subject to conditions from chlorine sanitizing rinse steps (or other oxidizing chlorine containing compositions). The liquid or solid detergent composition beneficially contain a reducing agent that reacts with chlorine introduced in sanitizing rinse steps that follow detergent cleaning steps. Methods for ware washing using the detergent compositions with reducing agents and methods for reducing residual chlorine in a ware washing cycle are also provided.

BACKGROUND OF THE INVENTION

The use of low temperature ware washing has grown throughout the industrial market driven by a desire to reduce utility costs and simplify electrical installation requirements of the ware washing machine. In order to sanitize ware in a low temperature dish machine a sanitizing rinse is employed. Often the rinse provides about 50 ppm solution of chlorine to sanitize the ware during the rinse step. Examples of sanitizers can include chlorine, iodine, quaternary ammonium compounds, or the like. However, chlorine is most commonly used in dish machines as a sanitizing rinse step. In these dish machines (i.e. any type of dishwashing appliance) the use of chlorine can yield conditions that readily facilitate corrosion of the stainless steel on and in the machines. This negatively results in the decreased lifespan of the machines. The exposure of the machine to chlorine is increased as due to the water conservation in these machines, the rinse water containing chlorine is reused in the next wash cycle.

Often commercial dish machines are made with 304 stainless steel due to ease of machining, ease of cleaning, strength to hold up in rugged commercial kitchen environment, and comparatively low cost. While the stainless steel provides all these benefits, the metal is susceptible to chlorine corrosion in low temperature warewash conditions.

Generally, a ware washing cycle, namely a dishwasher, implements a hydraulic system including pumps, water lines, etc. for circulating water/fluid through spray arms or other water-distribution provisions for washing the ware therein in a continuous or intermittent manner. A typical ware washing procedure may include a wash program for circulating a use solution of a detergent composition onto the ware via the spray arms or other water-distribution provisions of the dish machine. Thereafter, a rinse cycle may be provided for circulating clean rinse water onto the ware via the same or different spray arms. At least a portion of the wash water and the rinse water can be heated to various predetermined levels (e.g., the wash water being heated to a temperature generally between about 120-140° F. or 150-165° F. for low or high temperature ware washing, respectively, and the rinse water to a temperature generally equal to or higher than 120° F. or 180° F. for low or high temperature ware washing, respectively, so as to improve the effectiveness and efficiency of the dish machine, while also ensuring, in the case of the rinse water, proper sanitization of the ware. In some embodiments, low temperature conditions can be below 120° F. Various rinse aids and/or sanitizing aids (e.g. chlorine) are usually added to the rinse water for facilitating removal of the detergent from the dishware and/or sanitizing the ware.

In commercial ware washing methods the detergent and rinsing steps may also recycle water from an earlier step. For example, a fluid circulation system in the dish machine may include a single fluid circuit. In some dish machines and methods of employing them, the wash/rinse water may be pumped/re-circulated by one or more pump assemblies, out of a wash tank to various water distribution provisions (e.g., wash spray arms and rinse spray arms) mounted in the dish machine for spraying the wash/rinse water, under pressure, onto the ware contained therein. In such embodiments, the dishwashing fluid collected in the wash tank of the dish machine may be re-circulated through the water distribution provisions during each of the wash and rinse cycles that are typically implemented by the dish washer. In most instances the rinse water is reused in a subsequent wash cycle for the dish machine. As a result, there is residual chlorine from the sanitizing rinse that remains in contact with the dish machine during the ware washing.

In some commercial ware washing methods detergent and rinsing steps may be repeated. For example, a ware washing method may include a detergent step, a first rinse step, an additional detergent, an additional rinse step, etc. The rinse water may be collected in a wash tank of a dish machine and available for reuse, such as in a subsequent detergent step. As a result, there is residual chlorine from the sanitizing rinse that remains in contact with the dish machine during the ware washing.

In the event of these conditions where residual chlorine is in contact with the dish machine, there is a need for reducing the rate of corrosion that results from the chlorine concentration in contact with the stainless steel surfaces of the dish machine. It is therefore an object of this disclosure to provide compositions and methods to reduce the rate of and/or extent of corrosion on the stainless steel of the machines.

Conventional use of reducing agents or chlorine scavengers have been employed for treating water sources, e.g. to destroy chlorine in the water. Such use has also been documented in laundry applications where it is desirable to destroy chlorine in the laundering water. Various applications of reducing agents or chlorine scavengers are different from the need in sanitizing applications, where the level of chlorine bleach is significant (e.g. 50 ppm or more to provide sanitizing effect). Similarly reducing agents have been employed for enzyme stabilization in a wash solution, such as WO2006/013368, U.S. Pat. Nos. 4,421,664, and 3,741,901. However, such uses employ levels of these reducing agents and chlorine scavengers at substantially lower levels that do not impact corrosion and/or corrosion rates. In most uses the use levels of the reducing agents or chlorine scavengers do not exceed 5 ppm. In other uses such as U.S. Pat. No. 6,368,420, the reducing agents or chlorine scavengers are not included in a detergent composition. Such different formulations and use levels would be unable to overcome the level of oxidizers introduced in ware washing sanitizing methods, e.g. low temperature ware washing. Accordingly, there is a need for compositions and methods to reduce chlorine concentration in ware washing.

It is a further object of the disclosure to provide ware washing detergent compositions that contain a reducing agent to act as a corrosion inhibitor to the detergent itself, including in a normal dish washing cycle to counter act chlorine that is introduced from a preceding rinse cycle to decrease chlorine in the wash cycle.

It is another object of this disclosure to formulate ware washing detergent compositions that contain sodium bisulfite, sodium metabisulfite, or other chlorine reducing agent to overcome the challenges of chlorine concentrations in a normal dish washing cycle.

It is another object of the disclosure to provide compositions and methods of reducing corrosion in other industries and applications where chlorine-containing compositions contact stainless steel.

Other objects, aspects and advantages of this invention will be apparent to one skilled in the art in view of the following disclosure, the drawings, and the appended claims.

SUMMARY OF THE INVENTION

An advantage of the detergent compositions, methods of using the detergent compositions, methods of reducing residual chlorine (or other oxidizing chlorine containing compositions) in a ware washing cycle, and methods of reducing the rate of corrosion on a surface, is that chlorine (or other oxidizing chlorine containing compositions) concentration is reduced by the reducing agent and therefore not available to corrode surfaces, such as the stainless steel surfaces of a dish machine. Beneficially, as the reduction of available chlorine takes place during a wash cycle with the detergent composition containing the reducing agent, the lowered chlorine concentration does not negatively impact the sanitizing rinse cycle where the chlorine (or other oxidizing chlorine containing compositions) concentration is required. Instead, the detergent compositions and methods of employing the same reduce the available chlorine in the wash-step solution to lower the concentration of available chlorine and thus lower the corrosivity of the solution.

In embodiments a detergent composition comprises: a reducing agent that is a salt containing ammonium cation; an alkalinity source; and at least one additional functional ingredient comprising at least one builder, at least one water conditioning polymer, and/or at least one surfactant(s). In embodiments the reducing agent is a bisulfite in liquid or solid form, the alkalinity source comprises one or more of alkali metal hydroxides, alkali metal carbonates, alkali metal silicates, alkali metal salts, phosphates, and/or amines, the builder is a phosphonate, an aminocarboxylic acid, or a polyacrylate, the water conditioning polymer is a polycarboxylate, preferably a polyacrylic acid polymer and/or poly maleic acid polymer, and the surfactant is a nonionic surfactant. In embodiments, wherein the composition is a liquid, the reducing agent comprises from about 1 wt-% to about 10 wt-%, from about 1 wt-% to about 8 wt-%, or from about 2 wt-% to about 6 wt-% of the liquid composition, wherein the alkalinity source comprises from about 20 wt-% to about 60 wt-%, from about 25 wt-% to about 60 wt-%, or from about 30 wt-% to about 50 wt-% of the liquid composition, and wherein the additional functional ingredient(s) comprises from about 0.1 wt-% to about 60 wt-%, from about 0.1 wt-% to about 55 wt-%, or from about 0.1 wt-% to about 40 wt-% of the liquid composition. In preferred embodiments, the additional functional ingredient(s) in the liquid composition comprise at least one builder in the amount from about 1 wt-% to about 40 wt-%, or about 1 wt-% to about 5 wt-%, and/or at least one water conditioning agent in the amount from about 1 wt-% to about 10 wt-%, or about 2 wt-% to about 5 wt-%.

In additional embodiments wherein the composition is a solid, the reducing agent comprises from about 1 wt-% to about 10 wt-%, from about 1 wt-% to about 8 wt-%, or from about 2 wt-% to about 6 wt-% of the solid composition, wherein the alkalinity source comprises from about 40 wt-% to about 90 wt-%, from about 50 wt-% to about 90 wt-%, or from about 50 wt-% to about 80 wt-% of the solid composition, and wherein the additional functional ingredient(s) comprises from about 0.1 wt-% to about 70 wt-%, from about 0.1 wt-% to about 60 wt-%, or from about 0.1 wt-% to about 40 wt-% of the solid composition. In preferred embodiments, the additional functional ingredient(s) in the solid composition comprise at least one builder in the amount from about 1 wt-% to about 40 wt-%, or about 1 wt-% to about 5 wt-%, water conditioning agent(s) in the amount from about 1 wt-% to about 10 wt-%, or about 2 wt-% to about 8 wt-%, and/or surfactant(s) in the amount from about 0.1 wt-% to about 10 wt-%, or about 1 wt-% to about 5 wt-%.

In various embodiments, the reducing agent comprises from about 10 ppm to about 100 ppm, from about 10 ppm to about 90 ppm, from about 10 ppm to about 80 ppm, from about 10 ppm to about 70 ppm, from about 10 ppm to about 60 ppm, or from about 10 ppm to about 50 ppm of the composition in a use solution.

In embodiments, methods of cleaning using a detergent composition that reduces residual chlorine in a ware washing cycle, comprise: applying a use solution of the detergent composition as described herein to ware in a ware washing machine; and thereafter applying a chlorine sanitizing composition to ware in a ware washing machine; wherein the use solution of the detergent composition reuses water from a prior chlorine-containing sanitizing rinse step and comprises chlorine, and wherein the method reduces residual chlorine in the ware washing cycle. According to embodiments, the use solution of the detergent composition is diluted with water reused from a rinse cycle comprising chlorine. According to additional embodiments, the water used to generate the use solution of the detergent composition and/or rinsing ware with the chlorine sanitizing composition are heated to a temperature of at least about 120° F., or between about 120-140° F. In the various embodiments, the use solution of the detergent composition comprises from about 10 ppm to about 100 ppm, from about 10 ppm to about 90 ppm, from about 10 ppm to about 80 ppm, from about 10 ppm to about 70 ppm, from about 10 ppm to about 60 ppm, or from about 10 ppm to about 50 ppm of the reducing agent. In preferred embodiments, the use solution of the detergent composition comprises a sufficient concentration (ppm) of the reducing agent to reduce at least half of the residual chlorine in the use solution.

In additional embodiments, a method of reducing residual chlorine in a ware washing cycle comprises: applying a chlorine sanitizing composition to ware in a ware washing machine to provide a sanitizing step; reusing water from the sanitizing step to apply a use solution of a liquid or solid detergent composition and/or a booster composition to ware in a new wash cycle of the ware washing machine, wherein at least one of the liquid or solid detergent or the booster composition comprises a reducing agent; and reducing a residual chlorine concentration in the reused water for the detergent step. In embodiments, the residual chlorine concentration is reduced by at least about 50% or more. In embodiments, the use solution of the detergent composition and/or the booster composition comprises from about 10 ppm to about 100 ppm reducing agent, from about 20 ppm to about 80 ppm reducing agent, from about 20 ppm to about 60 ppm reducing agent, or from about 20 ppm to about 50 ppm reducing agent. In preferred embodiments, the use solution of the detergent composition and/or the booster composition comprises a sufficient concentration (ppm) of the reducing agent to reduce at least half of the residual chlorine in the use solution.

In additional embodiments, a method of reducing the rate of corrosion on a surface comprising, contacting a surface with a sanitizing composition comprising chlorine; contacting a surface with a use solution of a liquid or solid detergent composition and/or a booster composition comprising a reducing agent, wherein the reducing agent decreases the concentration of residual chlorine from the sanitizing composition; and reducing the rate of corrosion of the surface. In embodiments, the surface is metal, namely stainless steel. In embodiments, the surface is a ware washing machine. In preferred embodiments, the use solution of the detergent composition and/or the booster composition comprises from about 10 ppm to about 100 ppm reducing agent, from about 20 ppm to about 80 ppm reducing agent, from about 20 ppm to about 60 ppm reducing agent, or from about 20 ppm to about 50 ppm reducing agent. In still further embodiments, the use solution of the detergent composition and/or the booster composition comprises a sufficient concentration (ppm) of the reducing agent to reduce at least half of the residual chlorine in the use solution. In embodiments, the rate of corrosion on the surface is decreased as a result of the residual chlorine concentration is reduced by at least about 50% or more.

In additional embodiments, a ware washing system comprises: a detergent composition as described herein, optionally a booster composition comprising a reducing agent; and a chlorine sanitizing rinse composition. The system can further comprise a ware washing machine.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
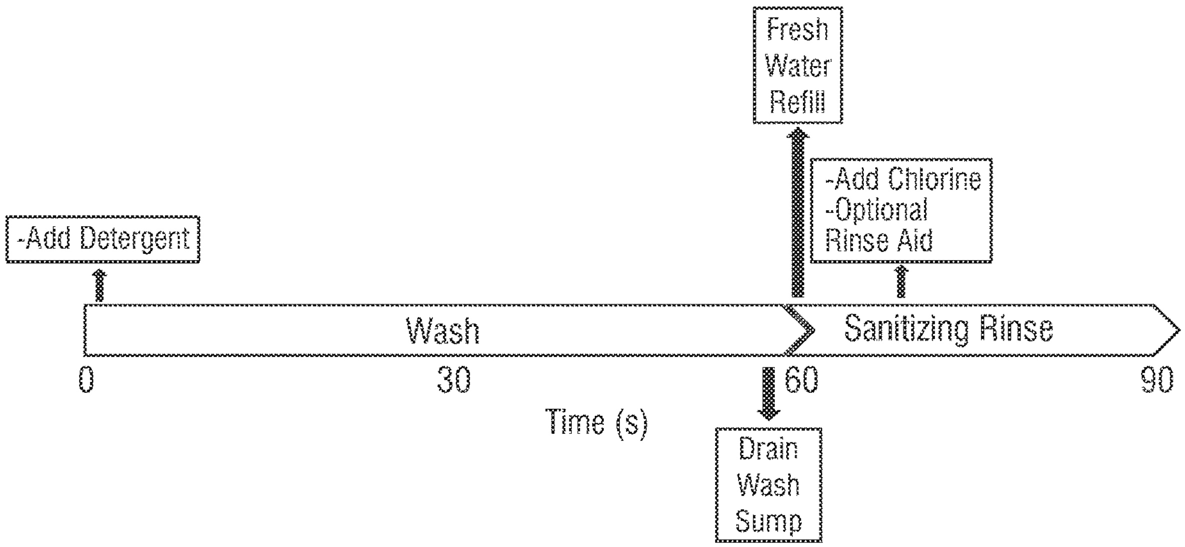
FIG. 1 shows a typical low temperature ware washing cycle, where water from the sanitizing rinse step is carried over and reused in the next cycle's wash step.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENTS

The embodiments are not limited to particular detergent compositions and methods of employing the same, which can vary and are understood by skilled artisans. It has been surprisingly found that the detergent compositions comprising a reducing agent beneficially reduce the rate of corrosion of ware washing machines (i.e. dish machines) through removal of residual chlorine (or other oxidizing chlorine containing compositions) that may be introduced, such as from residual water from a sanitizing rinse step.

It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers within the defined range. Throughout this disclosure, various aspects are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments without undue experimentation, but the preferred materials and methods are described herein. In describing and claiming the embodiments, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, "corrosion" refers to a loss in mass of a surface, namely metal surfaces which can vary in its susceptibility to chlorine (or other oxidizing chlorine containing compositions) corrosion. Corrosion can include localized (pitting) and general corrosion, each of which can be visually assessed through surface examination or quantified, such as through weight loss balance. X-ray diffraction can also be used to identify and assess corrosion through spectral analysis to identify chemical formulas for corroded metals in order to assess the change in state of metal as a result of corrosion. Corrosion can be measured by mass or area of a surface (e.g. stainless steel) with visible corrosion over a desired period of time (e.g. over repeated cycle running). Beneficially the detergent compositions result in a decrease in corrosion (or no corrosion), including as can be measured by mass loss from a surface, compared to controls compositions.

As used herein, the term "free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "surfactant" or "surface active agent" refers to an organic chemical that when added to a liquid changes the properties of that liquid at a surface.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions may comprise, consist essentially of, or consist of the components and ingredients as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Detergent Compositions

According to embodiments, the detergent compositions include an alkalinity source, a reducing agent, and additional functional ingredients for the ware washing or other types of formulations. Exemplary concentrate liquid detergent compositions are shown in Table 1 and concentrate solid detergent compositions are shown in Table 2 in weight percentages.

TABLE 1

| Liquid compositions | | | |
|---|---|---|---|
| Material | First Exemplary Range wt.-% | Second Exemplary Range wt.-% | Third Exemplary Range wt.-% |
| Reducing agent | 1-10 | 1-8 | 2-6 |
| Alkalinity source(s) | 20-60 | 25-60 | 30-50 |
| Water | 20-80 | 20-60 | 30-50 |
| Additional Functional Ingredients (e.g. chelants/builders, water conditioning agents, polymers, surfactants, etc.) | 0.1-60 | 1-55 | 1-50 |

TABLE 2

| Solid compositions | | | |
|---|---|---|---|
| Material | First Exemplary Range wt.-% | Second Exemplary Range wt.-% | Third Exemplary Range wt.-% |
| Reducing agent | 1-10 | 1-8 | 2-6 |
| Alkalinity source(s) | 40-90 | 50-90 | 50-80 |
| Additional Functional Ingredients (e.g. chelants/builders, water conditioning agents, polymers, surfactants, enzymes, etc.) | 0.1-50 | 1-40 | 1-30 |

Reducing Agent

The detergent compositions comprise at least one reducing agent. As described herein reducing agents decrease chlorine (or other oxidizing chlorine containing compositions) concentration that causes corrosion damage on metals, namely stainless steel surfaces, are included in a composition. As referred to herein, the reducing agent is suitable for reducing chlorine, $Cl_2$, HClO or other oxidizing chlorine containing compositions. The reducing agents are particularly well suited for chlorine reduction which his known to be far more corrosive than non-chlorine oxidizers (e.g. peroxide or peroxy species). However, it is not intended to limit the scope of the efficacy of the reducing agents, which may also be effective against non-chlorine oxidizers.

Examples of reducing agents are salts containing ammonium cations. Examples can include sulfite, sulfate, bisulfite, bisulfate, thiosulfite, thiosulfate, iodide, nitrate, chloride, borate, etc., antioxidants like carbonate, bicarbonate, percarbonate, perborate, sodium perborate tetrahydrate, sodium perborate monohydrate, carbamate, ascorbate, ascorbic acid or derivatives thereof, etc., organic amines such as ethylenediaminetetracetic acid (EDTA) or alkali metal salt thereof and monoethanolamine (MEA), and mixtures thereof. Additional examples can include phosphate, condensed phosphate, acetate, benzoate, citrate, formate, lactate, malate, tartrate, salicylate, ammonium, sulfite, bisulfite, aluminum tristearate, sodium silicate, benzotriazole, amines, amino acids, and mixtures thereof In an embodiment, a preferred reducing agent is a bisulfite in liquid or solid form.

In some embodiments, the reducing agent is included in the detergent composition at an amount of at least about 0.1 wt-% to about 20 wt-%, about 1 wt-% to about 15 wt-%, about 1 wt-% to about 10 wt-%, about 1 wt-% to about 8 wt-%, about 2 wt-% to about 8 wt-%, about 1 wt-% to about 7 wt-%, about 2 wt-% to about 7 wt-%, or about 2 wt-% to about 6 wt-%. In addition, without being limited according to the invention, all ranges recited are inclusive of the numbers defining the range and include each integer within the defined range.

The amount of reducing agent can vary according to its reaction rate with chlorine (or other oxidizing chlorine containing compositions), namely how many ppm of the reducing agent react with a ppm of available chlorine (or other oxidizing chlorine containing compositions). As one skilled in the art will ascertain from the disclosure herein, the reducing agent is provided in sufficient quantity to reduce at least half of the residual chlorine in the use solution. In preferred embodiments the reducing agent is included in an amount from about 0.1 wt-% to about 20 wt-% (or from about 1,000 to 200,000 ppm), from about 1 wt-% to about 15 wt-% (or from about 10,000 to 150,000 ppm), or more preferably from about 1 wt-% to about 10 wt-% (or from about 10,000 to 100,000 ppm). Alkalinity Source(s)

The detergent compositions comprise one or more alkalinity sources. The source of alkalinity can be any source of alkalinity that is compatible with the other components of the detergent composition. Exemplary sources of alkalinity include alkali metal hydroxides, alkali metal carbonates, alkali metal silicates, alkali metal salts, phosphates, amines, and mixtures thereof. In an exemplary liquid detergent composition a single alkalinity source may be included, whereas in solid detergent compositions a combination of different alkalinity sources may be preferred.

In an embodiment, preferred alkalinity sources include alkali metal hydroxides including sodium hydroxide, potassium hydroxide, and lithium hydroxide or mixtures thereof, and most preferred being sodium hydroxide and/or potassium hydroxide. In a further embodiment, preferred alkalinity sources include alkali metal carbonates including sodium carbonate. In still further embodiments, preferred alkalinity sources include a combination of alkali metal hydroxides including sodium hydroxide, potassium hydroxide, and lithium hydroxide or mixtures thereof, and most preferred being sodium hydroxide and/or potassium hydroxide, in combination with alkali metal carbonates including sodium carbonate.

In liquid detergent composition embodiments, the alkalinity source is included in an amount of at least about 20 wt-% to about 70 wt-%, about 20 wt-% to about 60 wt-%, about 25 wt-% to about 60 wt-%, about 30 wt-% to about 60 wt-%, about 30 wt-% to about 50 wt-%, or about 40 wt-% to about 50 wt-%. In addition, without being limited according to the invention, all ranges recited are inclusive of the numbers defining the range and include each integer within the defined range.

In solid detergent composition embodiments, the alkalinity source is included in an amount of at least about 40 wt-% to about 90 wt-%, about 50 wt-% to about 90 wt-%, about 50 wt-% to about 85 wt-%, about 50 wt-% to about 80 wt-%, about 55 wt-% to about 80 wt-%, or about 60 wt-% to about 80 wt-%. In addition, without being limited according to the invention, all ranges recited are inclusive of the numbers defining the range and include each integer within the defined range.

Additional Functional Ingredients

The components of the detergent composition can further be combined with various functional components suitable for uses disclosed herein, including ware washing detergents. In some embodiments, the detergent compositions including the reducing agent, alkalinity sources, water and/or hardening agents, further include at least one additional functional ingredient, at least two additional functional ingredients, or more.

The additional functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. For example, many of the functional materials discussed below relate to materials used in cleaning. However, other embodiments may include functional ingredients for use in other applications.

In some embodiments, the detergent compositions include a builder (sequestrants/chelating agents), water conditioning polymers, surfactants, enzymes, defoaming agents, antiredeposition agents, bleaching agents, solubility modifiers, dispersants, metal protecting agents, soil antiredeposition agents, stabilizing agents and/or processing aids, corrosion inhibitors, aesthetic enhancing agents including fragrances and/or dyes, additional rheology and/or solubility modifiers or thickeners, hydrotropes or couplers, buffers, solvents, additional cleaning agents and the like.

According to embodiments, the various additional functional ingredients may be provided in the detergent composition in the amount from about 0 wt-% and about 70 wt-%, from about 0 wt-% and about 60 wt-%, from about 0 wt-% and about 55 wt-%, from about 0 wt-% and about 50 wt-%, from about 0 wt-% and about 45 wt-%, or from about 0 wt-% and about 40 wt-%. According to further embodiments, the various additional functional ingredients may be included in the detergent compositions in the amount from about 0.1 wt-% and about 70 wt-%, from about 0.1 wt-% and about 60 wt-%, from about 0.1 wt-% and about 55 wt-%, or from about 0.1 wt-% and about 40 wt-%. In addition, without being limited according to the invention, all ranges recited are inclusive of the numbers defining the range and include each integer within the defined range.

Chelants/Builders

In an embodiment, the detergent compositions include one or more building agents, also called chelating or sequestering agents (e.g., chelants, builders or complexing agents), including, but not limited to: a phosphonate, an aminocarboxylic acid, or a polyacrylate. In general, a chelating agent is a molecule capable of coordinating (i.e., binding) the metal ions commonly found in natural water to prevent the metal ions from interfering with the action of the other detersive ingredients of a cleaning composition.

Examples of phosphonate builders include, but are not limited to: 2-phosphinobutane-1,2,4-tricarboxylic acid (PBTC) also referred to as phosphonobutane tricarboxylic acid (PBTC), 1-hydroxyethane-1,1-diphosphonic acid, $CH_2C(OH)[PO(OH)_2]_2$; aminotri(methylenephosphonic acid), $N[CH_2PO(OH)_2]_3$; aminotri(methylenephosphonate) sodium salt (ATMP), $N[CH_2{\cdot}2PO(ONa)_2]_3$; 2-hydroxyethyliminobis(methylenephosphonic acid), $HOCH_2CH_2N[CH_2PO(OH)_2]_2$; diethylenetriaminepenta(methylenephosphonic acid), $(HO)_2POCH_2N[CH_2CH_2N[CH_2PO(OH)_2]_2]_2$; diethylenetriaminepenta(methylenephosphonate), sodium salt (DTPMP); hexamethylenediamine(tetramethylenephosphonate), potassium salt; bis(hexamethylene)triamine(pentamethylenephosphonic acid); and phosphorus acid. Preferred phosphonates are PBTC, HEDP, ATMP and DTPMP. A neutralized or alkali phosphonate, or a combination of the phosphonate with an alkali source prior to being added into the mixture such that there is little or no heat or gas generated by a neutralization reaction when the phosphonate is added is preferred.

Detergent compositions can also (in addition) or in the alternative include a non-phosphate based builder. Although various components may include trace amounts of phosphorous, carboxylates such as citrate, tartrate or gluconate are also suitable. Useful aminocarboxylic acid materials containing little or no NTA include, but are not limited to:

N-hydroxyethylaminodiacetic acid, ethylenediaminetetraacetic acid (EDTA) (including tetrasodium EDTA), hydroxyethylenediaminetetraacetic acid, diethylenetriaminepentaacetic acid, N-hydroxyethyl-ethylenediaminetriacetic acid (HEDTA), diethylenetriaminepentaacetic acid (DTPA), hydroxyethylethylenediaminetriacetic acid and methylglycinediacetic acid (MGDA), glutamic acid-diacetic acid (GLDA), iminodisuccinic acid (IDA), hydroxyiminodisuccinic acid, ethylenediaminedisuccinic acid (EDDS), aspartic acid-diacetic acid, and salts thereof. Particularly preferred building agents are MGDA and GLDA and salts thereof and/or other similar acids having an amino group with a carboxylic acid substituent.

In exemplary liquid or solid detergent composition embodiments, the builder(s) is included in an amount of at least about 0.1 wt-% to about 50 wt-%, about 0.1 wt-% to about 40 wt-%, about 1 wt-% to about 35 wt-%, about 1 wt-% to about 30 wt-%, about 1 wt-% to about 20 wt-%, about 1 wt-% to about 10 wt-%, about 1 wt-% to about 5 wt-%, about 1 wt-% to about 4 wt-%, about 1 wt-% to about 3 wt-%, or about 1 wt-% to about 2 wt-%. In exemplary heavy duty liquid or solid detergent composition embodiments, the builder(s) can be included in an amount of at least about 0.1 wt-% to about 50 wt-%, about 0.1 wt-% to about 40 wt-%, about 1 wt-% to about 40 wt-%, about 5 wt-% to about 40 wt-%, about 10 wt-% to about 40 wt-%, or even about 15 wt-% to about 40 wt-%, or still further about 20 wt-% to about 40 wt-%. In addition, without being limited according to the invention, all ranges recited are inclusive of the numbers defining the range and include each integer within the defined range.

Water Conditioning Agent/Polymer

In an embodiment, the detergent compositions include one or more water conditioning agents/polymers, including, but are not limited to: polycarboxylates. Exemplary polycarboxylates that can be used as builders and/or water conditioning polymers include, but are not limited to: those having pendant carboxylate (—$CO2^-$) groups such as polyacrylic acid, maleic acid, polymaleic acid, polyacrylic/polymaleic acid blend (such as commercially-available as Acusol 448, available from Dow Inc), maleic acid/polymaleic acid blend (such as commercially available as Belclene 200, available from BWA Water Additives), maleic/olefin copolymer, sulfonated copolymer or terpolymer, acrylic/maleic copolymer, acrylic homopolymers (such as commercially available as Acumer 1000, available from Dow Chemical), polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, and hydrolyzed acrylonitrile-methacrylonitrile copolymers.

The polymers may also include water-soluble or water-insoluble substances, the main task of which consists in the binding of calcium and magnesium ions. These may be low molecular weight carboxylic acids and salts thereof, such as alkali metal citrates, especially anhydrous trisodium citrate or trisodium citrate dihydrate, alkali metal succinates, alkali metal malonates, fatty acid sulfonates, oxidisuccinate, alkyl or alkenyl disuccinates, gluconic acids, oxadiacetates, carboxymethyloxysuccinates, tartrate monosuccinate, tartrate disuccinate, tartrate monoacetate, tartrate diacetate and a-hydroxypropionic acid.

In a preferred embodiment, the water conditioning agent/polymer is a polymaleic acid, a polyacrylic acid, or a combination thereof, such as a copolymer of poly maleic acid and polyacrylic acid. A further preferred water conditioning agent/polymer is an acrylic homopolymer. A further preferred water conditioning agent/polymer is a polymaleic acid or maleic acid/polymaleic acid. In preferred embodiments, one or more of these preferred water conditioning agent/polymer(s) is included in the liquid or solid detergent compositions containing the reducing agent.

In exemplary liquid detergent composition embodiments, the water conditioning agent/polymer(s) is included in an amount of at least about 0.1 wt-% to about 10 wt-%, about 0.5 wt-% to about 10 wt-%, about 1 wt-% to about 10 wt-%, about 0.5 wt-% to about 5 wt-%, about 1 wt-% to about 10 wt-%, about 1 wt-% to about 5 wt-%, or about 2 wt-% to about 5 wt-%. In addition, without being limited according to the invention, all ranges recited are inclusive of the numbers defining the range and include each integer within the defined range.

In solid detergent composition embodiments, water conditioning agent/polymer(s) is included in an amount of at least 0.1 wt-% to about 10 wt-%, about 0.5 wt-% to about 10 wt-%, about 1 wt-% to about 10 wt-%, about 0.5 wt-% to about 5 wt-%, about 1 wt-% to about 10 wt-%, about 1 wt-% to about 5 wt-%, or about 2 wt-% to about 5 wt-%. In addition, without being limited according to the invention, all ranges recited are inclusive of the numbers defining the range and include each integer within the defined range.

Dispersants

In some embodiments, the detergent compositions include one or more dispersants. Dispersants, including dispersant polymers, disperse inorganic and organic soils in the warewash applications (and other applications).

In exemplary liquid detergent composition embodiments, the dispersant is included in an amount of at least about 0 wt-% to about 5 wt-%, about 0 wt-% to about 3 wt-%, or about 0 wt-% to about 2 wt-%. In solid detergent composition embodiments, the surfactant(s) is included in an amount of at least 0.1 wt-% to about 10 wt-%, about 1 wt-% to about 10 wt-%, about 1 wt-% to about 5 wt-%, or about 2 wt-% to about 5 wt-%. In addition, without being limited according to the invention, all ranges recited are inclusive of the numbers defining the range and include each integer within the defined range.

Surfactants

In some embodiments, the detergent compositions include one or more surfactants. Surfactants suitable for use with the compositions include, but are not limited to, nonionic surfactants, cationic surfactants, and anionic surfactants. Surfactants can be included in the compositions for soil removal, sheeting performance and/or defoaming.

In exemplary liquid detergent composition embodiments, the surfactant(s) is included in an amount of at least about 0 wt-% to about 5 wt-%, about 0 wt-% to about 3 wt-%, or about 0 wt-% to about 2 wt-%. In solid detergent composition embodiments, the surfactant(s) is included in an amount of at least 0.1 wt-% to about 10 wt-%, about 1 wt-% to about 10 wt-%, about 1 wt-% to about 5 wt-%, or about 2 wt-% to about 5 wt-%. In addition, without being limited according to the invention, all ranges recited are inclusive of the numbers defining the range and include each integer within the defined range.

Nonionic Surfactants

Suitable nonionic surfactants suitable for use with the compositions include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC11; mixtures thereof, or the like.

The semi-polar type of nonionic surface active agents is another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

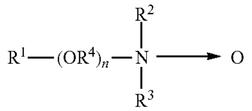

wherein the arrow is a conventional representation of a semi-polar bond; and $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N-($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula: R—O—$(CH_2CH_2O)_n(CH_2)_m$ to about $CO_2X$ (3)

in which R is a $C_8$ to $C_{22}$ alkyl group or

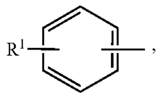

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

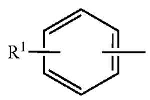

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Cationic Surfactants

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

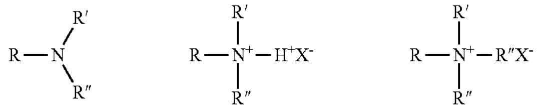

in which, R represents a long alkyl chain, R', R'', and R''' may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those or skill in the art and described in "Surfactant Encyclopedia", *Cosmetics & Toiletries*, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions of the present invention include those having the formula $R^1_m R^2_x Y_L Z$ wherein each $R^1$ is an organic group containing a straight or branched alkyl or alkenyl group optionally substituted with up to three phenyl or hydroxy groups and optionally interrupted by up to four of the following structures:

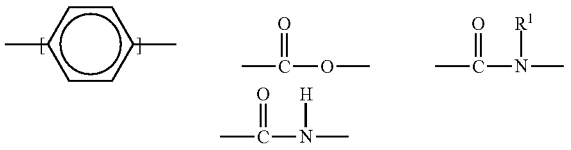

or an isomer or mixture of these structures, and which contains from about 8 to 22 carbon atoms. The $R^1$ groups can additionally contain up to 12 ethoxy groups. m is a number from 1 to 3. Preferably, no more than one $R^1$ group in a molecule has 16 or more carbon atoms when m is 2 or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group are filled by hydrogens. Y can be a group including, but not limited to:

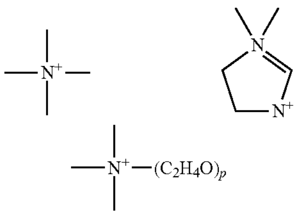

p = about 1 to 12

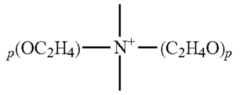

p = about 1 to 12

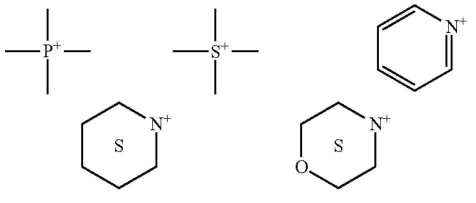

or a mixture thereof. Preferably, L is 1 or 2, with the Y groups being separated by a moiety selected from $R^1$ and $R^2$ analogs (preferably alkylene or alkenylene) having from 1 to about 22 carbon atoms and two free carbon single bonds when L is 2. Z is a water soluble anion, such as a halide, sulfate, methylsulfate, hydroxide, or nitrate anion, particularly preferred being chloride, bromide, iodide, sulfate or methyl sulfate anions, in a number to give electrical neutrality of the cationic component.

Methods of Use

The methods of use can include methods of ware washing, methods of reducing residual chlorine (or other oxidizing chlorine containing compositions) in a ware washing cycle, methods of reducing residual chorine in other applications (e.g. non-ware washing), and methods of reducing the rate of corrosion on a surface. The detergent compositions comprising a reducing agent are particularly well suited for use in ware washing applications, including consumer and/or institutional ware washing. Exemplary ware washing equipment includes, for example, low temperature dish machines (as use of chlorine sanitizers is often employed), industrial dish machines including automatic dishwashing or ware-washing machines, door-style or hood-style machines, and any other machines made of stainless steel. In most instances consumer or homestyle dish machines are not made of stainless steel and therefore do not require the same reduction of corrosion on the surfaces as described herein.

The methods can also be used in non-ware washing applications. For example, any consumer and/or institutional process where a chlorine-containing sanitizer (or other oxidizing chlorine containing compositions) is applied to a stainless steel surface that can benefit from the compositions and methods described herein.

The detergent composition can be applied to ware using any conventional methods. For example, most dishwashers have a hydraulic system including pumps, water lines, etc. for circulating water/fluid through spray arms or other water-distribution provisions for washing the ware therein in a continuous or intermittent manner. In many embodiments, a detergent use solution is circulated onto the ware via the spray arms or other water-distribution provisions of the dish machine. Thereafter, the water from the detergent wash cycle is drained and a rinse cycle is provided for circulating clean rinse water onto the ware via the same or different spray arms.

In ware washing applications, the detergent composition can be provided as a liquid or a solid composition. A use solution of the detergent composition is generally in contact with the ware in need of cleaning for a sufficient amount of time to clean the ware. In institutional ware washing cycles this can be about 60 seconds. In an aspect, the ware (or other surface or object) is contacted with the detergent composition for at least about 1 minute. In other aspects, such as consumer use, the ware (or other surface or object) is contacted with the detergent composition for at least about at least about 1 minute, 10 minutes, between about 10 minutes and about 20 minutes, or longer. As the water used to dilute the detergent composition to provide the use solution onto the ware during the cycle often employs water reused from a prior rinse cycle, this water may contain chlorine (or other oxidizing chlorine containing compositions) at a concentration that is undesirable as it causes corrosion to the metal surfaces in the dish machine. During the washing cycle the detergent composition containing the reducing agent beneficially reduces the residual chlorine concentration (or other oxidizing chlorine containing compositions) to reduce the rate of any corrosion seen on the metal surfaces of the dish machine.

In an embodiment, a use concentration of the deterrent composition includes from about 200 ppm to about 5,000 ppm, or from about 600 ppm to about 3,000 ppm, or from about 800 ppm to about 2,000 ppm, including all ranges therebetween.

The reducing agent is provided in the range from about 10 ppm to about 100 ppm, from about 10 ppm to about 90 ppm, or from about 10 ppm to about 80 ppm, from about 10 ppm to about 70 ppm, from about 10 ppm to about 60 ppm, or from about 10 ppm to about 50 ppm, including all ranges therebetween. In other embodiments the reducing agent is provided in the range of from about 25 ppm to about 100 ppm, from about 25 ppm to about 90 ppm, from about 25 ppm to about 80 ppm, from about 25 ppm to about 70 ppm, from about 25 ppm to about 60 ppm, or from about 25 ppm to about 50 ppm of the composition in a use solution. In additional embodiments, the methods described herein can alternatively be achieved through use of a booster composition comprising the reducing agent (instead of or in addition to the reducing agent in the detergent composition). As one skilled in the art will ascertain a booster composition can provide the reducing agent to the wash water in the warewashing application when a reformulation of a liquid or solid detergent composition is not desired or available. The methods can then still benefit from the dosing of the reducing agent to reduce residual chlorine (or other oxidizing chlorine containing compositions) in a ware washing cycle, reduce residual chorine in other applications (e.g. non-ware washing), and reduce the rate of corrosion on a surface.

At least a portion of the wash water and the rinse water can be heated to various predetermined levels. In low temperature ware wash embodiments, the wash water can be heated to a temperature generally around 120° F., or between 120-140° F. and the rinse water can be heated to a temperature generally equal to or higher than 120° F. In high temperature ware wash embodiments, the wash water can be heated to a temperature generally higher than 150-165° F. and the rinse water can be heated to a temperature generally equal to or higher than 180° F. The heating of the water improves the effectiveness and efficiency of the dish machine, while also ensuring, in the case of the rinse water, proper sanitization of the ware. The use of the detergent compositions described herein in a ware washing cycle is particularly useful in low temperature cycles where a sanitizing rinse step is included.

The methods described herein are particularly beneficial for reducing chlorine concentration during the wash cycle where the detergent composition is contacting the ware. In an embodiment, the detergent composition reduces residual chlorine concentration carried forward into the wash cycle by at least about 20%, 25%, 30%, 35%, 40%, 45%, 50%, 55%, 60%, or more. In a preferred embodiment, the detergent composition reduces residual chlorine concentration carried forward into the wash cycle by at least about 50%.

The methods described herein are particularly useful for reducing the rate of corrosion. In an embodiment corrosion rate measurements can be quantified through mass loss balance. This technique is suitable for both generalized and localized corrosion and can be described as follows. The tubular test coupons received a surface treatment after each electrochemical experiment in order to remove any corrosion product eventually deposited on the surface before being weighed. The test coupons are copiously rinsed with water, smoothly brushed, and then immersed into concentrated hydrochloric acid for 5 seconds. Finally, the test coupons are copiously rinsed with distilled water, dried, and weighed.

In embodiments, the detergent compositions result in a decrease of, decreased rate of, or elimination of corrosion as measured by mass loss balance in comparison to control formulations. In some embodiments the warewash detergent compositions with reducing agents do not exhibit mass loss over at least about 4 weeks, at least about 6 weeks, at least about 8 weeks, at least about 10 weeks, at least about 12 weeks or greater, as are indicative of a non-corrosive composition. In further embodiments the warewash detergent compositions provide a reduced rate of corrosion over time, including for periods of time of at least about 6 months, at least about 9 months, or at least about 12 months with a decreased rate of corrosion as measured by mass loss balance in comparison to controls.

Another way to quantify rate of corrosion is through linear polarization resistance technique (LPR). LPR is one of the most commonly used methods to measure corrosion rate. It is a DC electrochemical technique and is typically based on the imposition of a small voltage to the electrodes, (−10 mV to +10 mV) around the Open Circuit Potential (OCP). If the potential is raised above the free corrosion potential (Ecorr), the metal dissolution rate will increase. Conversely, if the potential is lowered, the rate will decrease. The LPR technique assumes that the exponential anodic (i.e. potential above Ecorr), and the cathodic (i.e. potential below Ecorr) polarization curves approximate to a straight line close to the free corrosion potential (OCP). The corrosion rate can then be derived from the theoretical Stern and Geary analysis of polarization curves and Faraday's Law.

In an embodiment the rate of corrosion as measured by one or more analytical techniques, is reduced by at least 50% (or the rate is cut in half). This is a result of the approximately a 100% increase in time to reach the same level of corrosion on a surface the reduction in chlorine concentration by the reducing agent in the detergent composition.

The present disclosure is further defined by the following numbered paragraphs:

1. A detergent composition comprising:
   a reducing agent that is a salt containing ammonium cation;
   an alkalinity source; and
   at least one additional functional ingredient comprising at least one builder, at least one water conditioning polymer, and/or at least one surfactant(s).
2. The composition of paragraph 1, wherein the reducing agent is a bisulfite in liquid or solid form.
3. The composition of any one of paragraphs 1-2, wherein the alkalinity source comprises one or more of alkali metal hydroxides, alkali metal carbonates, alkali metal silicates, \ alkali metal salts, phosphates, and/or amines.
4. The composition of paragraph 3, wherein the alkalinity source comprises one or more of alkali metal hydroxide and alkali metal carbonate.
5. The composition of any one of paragraphs 1-4, wherein the builder is a phosphonate, an aminocarboxylic acid, or a polyacrylate.
6. The composition of any one of paragraphs 1-5, wherein the water conditioning polymer is a polycarboxylate, preferably a polyacrylic acid polymer and/or poly maleic acid polymer.
7. The composition of any one of paragraphs 1-6, wherein the surfactant is a nonionic surfactant.
8. The composition of any one of paragraphs 1-7, wherein the composition is a liquid, and wherein the reducing agent comprises from about 1 wt-% to about 10 wt-%, from about 1 wt-% to about 8 wt-%, or from about 2 wt-% to about 6 wt-% of the liquid composition, wherein the alkalinity source comprises from about 20 wt-% to about 60 wt-%, from about 25 wt-% to about 60 wt-%, or from about 30 wt-% to about 50 wt-% of the liquid composition, and wherein the additional functional ingredient(s) comprises from about 0.1 wt-% to about 60 wt-%, from about 0.1 wt-% to about 55 wt-%, or from about 0.1 wt-% to about 40 wt-% of the liquid composition.
9. The composition of paragraph 8, wherein the additional functional ingredient(s) in the liquid composition comprise at least one builder in the amount from about 1 wt-% to about 40 wt-%, or about 1 wt-% to about 5 wt-%, and/or at least one water conditioning agent in the amount from about 1 wt-% to about 10 wt-%, or about 2 wt-% to about 5 wt-%.
10. The composition of any one of paragraphs 1-7, wherein the composition is a solid, and wherein the reducing agent comprises from about 1 wt-% to about 10 wt-%, from about 1 wt-% to about 8 wt-%, or from about 2 wt-% to about 6 wt-% of the solid composition, wherein the alkalinity source comprises from about 40 wt-% to about 90 wt-%, from about 50 wt-% to about 90 wt-%, or from about 50 wt-% to about 80 wt-% of the solid composition, and wherein the additional functional ingredient(s) comprises from about 0.1 wt-% to about 70 wt-%, from about 0.1 wt-% to about 60 wt-%, or from about 0.1 wt-% to about 40 wt-% of the solid composition.
11. The composition of paragraph 9, wherein the additional functional ingredient(s) in the solid composition comprise at least one builder in the amount from about 1 wt-% to about 40 wt-%, or about 1 wt-% to about 5 wt-%, water conditioning agent(s) in the amount from about 1 wt-% to about 10 wt-%, or about 2 wt-% to about 8 wt-%, and/or surfactant(s) in the amount from about 0.1 wt-% to about 10 wt-%, or about 1 wt-% to about 5 wt-%.
12. The composition of any one of paragraphs 1-11, wherein the reducing agent comprises from about 10 ppm to about 100 ppm, from about 10 ppm to about 90 ppm, from about 10 ppm to about 80 ppm, from about 10 ppm to about 70 ppm, from about 10 ppm to about 60 ppm, or from about 10 ppm to about 50 ppm of the composition in a use solution.
13. A method of cleaning using a detergent composition that reduces residual chlorine in a ware washing cycle, comprising:
   applying a use solution of the detergent composition of any one of paragraphs 1-12 to ware in a ware washing machine; and thereafter
   applying a chlorine sanitizing composition to ware in a ware washing machine;
   wherein the use solution of the detergent composition reuses water from a prior chlorine-containing sanitizing rinse step and comprises chlorine, and
   wherein the method reduces residual chlorine in the ware washing cycle.
14. The method of paragraph 13, wherein the use solution of the detergent composition is diluted with water reused from a rinse cycle comprising chlorine.
15. The method of any one of paragraphs 13-14, wherein the water used to generate the use solution of the detergent composition and/or rinsing ware with the chlorine sanitizing composition are heated to a temperature of at least about 120° F., or between about 120-140° F.
16. The method of any one of paragraphs 13-15, wherein the use solution of the detergent composition comprises from about 10 ppm to about 100 ppm, from about 10 ppm to about 90 ppm, from about 10 ppm to about 80 ppm, from about 10 ppm to about 70 ppm, from about 10 ppm to about 60 ppm, or from about 10 ppm to about 50 ppm of the reducing agent.
17. The method of any one of paragraphs 13-15, wherein the use solution of the detergent composition comprises a sufficient concentration (ppm) of the reducing agent to reduce at least half of the residual chlorine in the use solution.
18. A method of reducing residual chlorine in a ware washing cycle, comprising:
   applying a chlorine sanitizing composition to ware in a ware washing machine to provide a sanitizing step;
   reusing water from the sanitizing step to apply a use solution of a liquid or solid detergent composition and/or a booster composition to ware in a new wash cycle of the ware washing machine, wherein at least one of the liquid or solid detergent or the booster composition comprises a reducing agent; and reducing a residual chlorine concentration in the reused water for the detergent step.

19. The method of paragraph 18, wherein the residual chlorine concentration is reduced by at least about 50% or more.

20. The method of any one of paragraphs 18-19, wherein the use solution of the detergent composition and/or the booster composition comprises from about 10 ppm to about 100 ppm reducing agent, from about 20 ppm to about 80 ppm reducing agent, from about 20 ppm to about 60 ppm reducing agent, or from about 20 ppm to about 50 ppm reducing agent.

21. The method of any one of paragraphs 18-19, wherein the use solution of the detergent composition and/or the booster composition comprises a sufficient concentration (ppm) of the reducing agent to reduce at least half of the residual chlorine in the use solution.

22. A method of reducing the rate of corrosion on a surface, comprising:

contacting a surface with a sanitizing composition comprising chlorine;

contacting a surface with a use solution of a liquid or solid detergent composition and/or a booster composition comprising a reducing agent, wherein the reducing agent decreases the concentration of residual chlorine from the sanitizing composition; and reducing the rate of corrosion of the surface.

23. The method of paragraph 22, wherein the surface is metal.

24. The method of paragraph 23, wherein the metal is stainless steel.

25. The method of any one of paragraphs 22-24, wherein the surface is a ware washing machine.

26. The method of any one of paragraphs 22-25, wherein the use solution of the detergent composition and/or the booster composition comprises from about 10 ppm to about 100 ppm reducing agent, from about 20 ppm to about 80 ppm reducing agent, from about 20 ppm to about 60 ppm reducing agent, or from about 20 ppm to about 50 ppm reducing agent.

27. The method of any one of paragraphs 22-25, wherein the use solution of the detergent composition and/or the booster composition comprises a sufficient concentration (ppm) of the reducing agent to reduce at least half of the residual chlorine in the use solution.

28. The method of any one of paragraphs 22-27, wherein the rate of corrosion on the surface is decreased as a result of the residual chlorine concentration is reduced by at least about 50% or more.

29. A ware washing system comprising:

a detergent composition according to any one of paragraphs 1-12, optionally a booster composition comprising a reducing agent; and a chlorine sanitizing rinse composition.

30. The system of paragraph 29, further comprising a ware washing machine.

Having thus described in detail various embodiments of the present disclosure, it is to be understood that the present disclosure defined by the above numbered paragraphs is not to be limited to particular details set forth in the above description as many apparent variations thereof are possible without departing from the spirit or scope of the present disclosure.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

The methods of ware washing in a typical low temperature ware washing cycle, as depicted in FIG. 1, where water from the sanitizing rinse step is carried over and reused in the next cycle's wash step was employed in evaluating the effect of a detergent composition comprising a reducing agent on residual chlorine concentration. The evaluated liquid detergent compositions are shown in Table 3.

TABLE 3

| Component | Liquid Control Detergent | Liquid Detergent with Reducing Agent |
|---|---|---|
| Water | 46.5 | 42.55 |
| Phosphonobutanetricarboxylic Acid, 50% | 2 | 2 |
| Polyacrylic Acid, 48% | 4 | 4 |
| Sodium hydroxide (NaOH), 50% | 47.5 | 47.5 |
| Sodium bisulfite solution, 38% | 0 | 3.95 |

The two evaluated liquid detergent compositions were analyzed through the ware washing cycles in a dishwashing machine. The testing used 11.4 grams of detergent composition per 1.5 gallons of wash water, of the 11.4 grams detergent composition, 0.171 grams is the reducing agent sodium bisulfite. At 60 seconds, the wash solution is dumped and replaced with fresh water, to which sufficient concentrated chlorine to make a 50 ppm solution is added. That solution carries forward to the next wash step when the detergent composition (Control or addition of reducing agent) is added at time 0 to a concentration of 2000 ppm. The solution with reducing agent at 30 ppm in solution significantly lowers the concentration of available chlorine.

Figure 2:
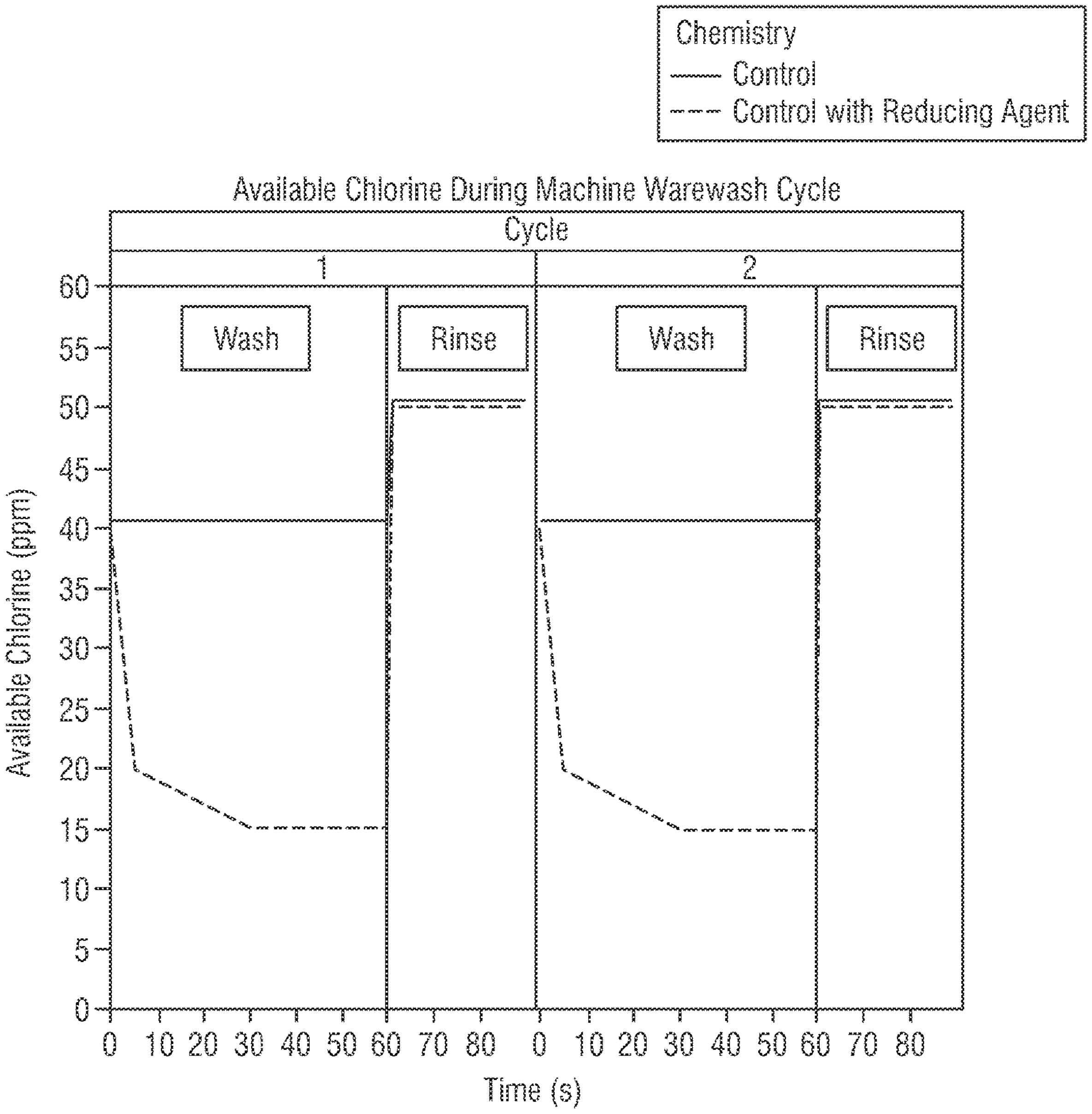
FIG. 2 shows a graph depicting concentration of available chlorine in solution of a dish machine during back-to-back cycles (as depicted in FIG. 1), where a Control detergent is compared to a detergent with reducing agent as described in Example 1.

FIG. 2 shows measured concentration of available chlorine in solution of the dish machine. The FIG. 2 shows an initial measurement of chlorine (which illustrates as method where the water is reused from the prior rinse cycle and introduces chlorine into the ware wash machine) and a near instantaneous reduction in chlorine the detergent with reducing agent for the 60 second wash cycle, before additional chlorine is introduced into with the rinse cycle with fresh water in the cycle for 30 additional seconds. The entire cycle in the commercial warewash cycle is approximately 90 seconds. The overall reduction of residual chlorine in the wash step from approximately 40 ppm down to 20 ppm at about 5-10 seconds and further down to about 15 ppm at 30-60 seconds provides a substantial decrease in chlorine concentration in contact with the stainless steel dish machine, beneficially providing a reduction in the rate of corrosion of the machine.

Visual assessments of corrosion on bolts inside of the dish machine door and the top of the dish machine door after 8000 cycles as described herein were made. An average commercial facility employing a low temperature dish machine runs about 2000 cycles per month; these observations were made after 4 months' testing to compare the detergent with reducing agent to the control detergent. The dish machine using the detergent with reducing agent at 30 ppm in solution exhibited significantly less corrosion than the control detergent. Quantifiable measurements of corrosion reduction will be made.

Example 2

Additional formulations containing the reducing agent were evaluated for warewashing efficacy while retaining benefits of reduced residual chlorine concentration. The evaluated liquid detergent composition is shown in Table 4. The test methods used a Hobart AM15 industrial warewash machine with a standard 1-minute cycle at 155-160° F. (high temperature, HT) with 20-25 psi rinse, 5 gpg water, and no background soils. The specifications of the Hobart AM15 warewash machine are as follows: Washbath volume: 53 L sump volume, Rinse volume: 2.8 L, Wash time: 50 sec., and Rinse time: 9 sec. The evaluated liquid detergent has a 30% chelant package (MGDA) to provide heavy duty performance in combination with the reducing agent. The evaluated ware washed according to the methods described herein were entrée plates for protein analysis. The methods included staining of the wares after each wash within 1-2 minutes and photographs taken immediately after. For the protein staining commassie blue solution was used and then rinse with de-stain solution.

TABLE 4

| Component | Liquid Detergent with Reducing Agent (wt-%) |
|---|---|
| Sodium hydroxide (NaOH), 50% | 30 |
| Polymers (Acumer 1000, 48%, Acusol 448, Belclene 200) | 5.9 |
| MGDA, 40% | 30 |
| Sodium bisulfite solution, 38% | 5.7 |
| Water | 28.4 |
| Total | 100 |

Figure 3:
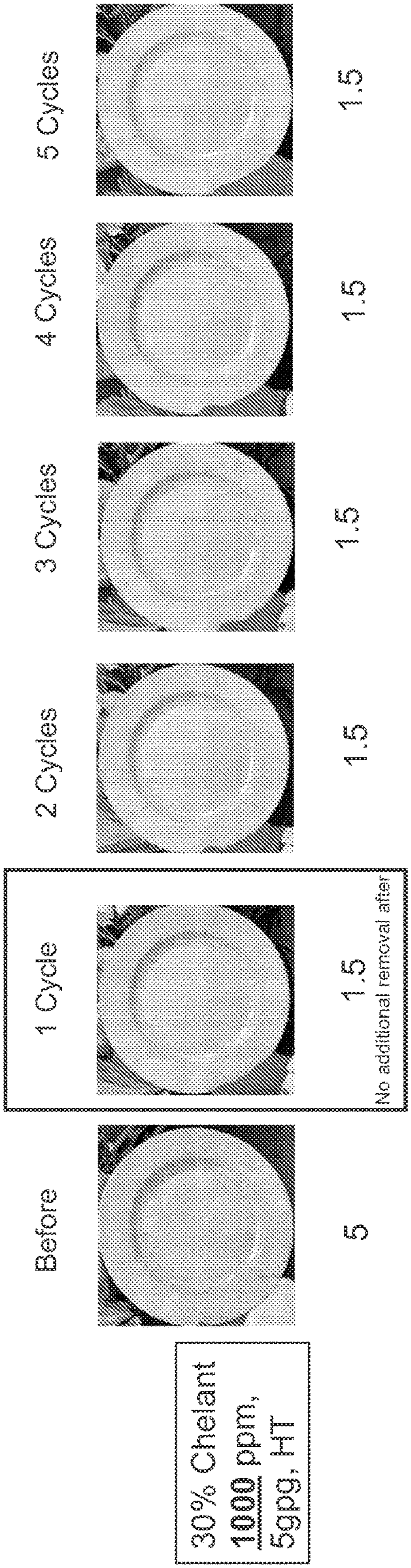
FIG. 3 shows a photograph depicting protein removal of a liquid detergent containing reducing agent as described in Example 2.

A visual rating on soil coverage percentage was used as follows: 5=100~75%; 4=75~50%; 3=50~25%; 2=25~1%; 1=<1%. The results are shown in FIG. 3, where a visual score of 1 was achieved after a first cycle through the warewash machine was achieved, demonstrating heavy duty performance with the detergent containing the reducing agent. After additional cycles (up to 5) no further removal detected; noting that the detergent was effective after a single warewash cycle. This shows that the formulation provides efficacious warewashing and the inclusion of the reducing agent, to provide further benefits of reducing residual chlorine in the warewash process when a sanitizing step is used (as demonstrated in Example 1), does not interfere with the warewash efficacy of the detergent.

Further evaluation of the liquid detergent containing the reducing agent shown in Table 4 was evaluated on 10 oz. Libbey glasses in a 100-cycle test in the same Hobart AM15 machine. The liquid detergent was tested at 2000 ppm detergent using 16 gpg water (1 grain=17 ppm). The test procedure evaluates detergent formulations to test glasses washed in an institutional warewash machine with a predetermined concentration of detergent. All of the glasses are left untreated and examined for film accumulation. 6 glasses were cleaned before testing. The dish machine was filled with the water (and water hardness measured). Tank heaters were turned on and the dish machine and wash/rinse cycles through the machine were completed at a wash temperature of 150-160° F. and rinse temperature of 175-190° F. A controller dispensed the desired amount of detergent into the wash tank (titrated to verify detergent concentration). The glasses were placed in a Raburn rack and placed inside the dish machine. At the beginning of each wash cycle, the appropriate amount of detergent composition to achieve the desired concentration was automatically dispensed into the warewash machine to maintain the initial detergent concentration. The glasses were dried overnight, and then the following visual numeric grades were assigned for film accumulation using a strong light source.

After the 100-cycle test, glasses can be analyzed using a lightbox test. The light box tests were not completed due to connectivity issues. However further (non-visual) assessments in addition to the results in FIG. 4 can be completed for analysis of film accumulation on glasses. The lightbox test standardizes the evaluation of the glasses run in the 100-cycle test using an analytical method. The lightbox test is based on the use of an optical system including a photographic camera, a lightbox, a light source and a light meter. The system is controlled by a computer program (Spot Advance and Image Pro Plus). For this testing each glass is placed on its side in the lightbox, and the intensity of the light source was adjusted to a predetermined value using a light meter. The conditions of the 100-cycle test were entered into the computer. A picture of the glass is taken with the camera and saved on the computer for analysis by the program. The picture is then analyzed using the upper half of the glass in order to avoid the gradient of darkness on the film from the top of the glass to the bottom of the glass, based on the shape of the glass. Generally, a lower lightbox rating indicates that more light was able to pass through the glass. Thus, the lower the lightbox rating, the more effective the composition was at preventing scaling on the surface of the glass. Light box evaluation of a clean, unused glass has a light box score of approximately 12,000 which corresponds to a score of 72,000 for the sum of six glasses. For further testing of the light box results a light box score differing by 10,000 is considered significant.

Figure 4:
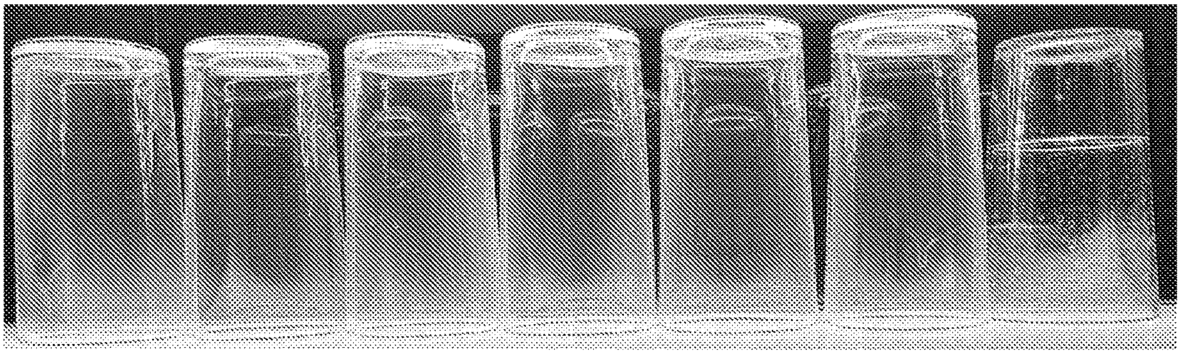
FIG. 4 shows a photograph depicting ware wash performance of a liquid detergent containing reducing agent as described in Example 2.

At this time the results of the 100-cycle test are shown in FIG. 4 (without lightbox quantification) where the glasses show efficacious warewashing and the inclusion of the reducing agent does not interfere with the warewash efficacy.

Example 3

Additional formulations containing the reducing agent were evaluated for warewashing efficacy while retaining benefits of reduced residual chlorine concentration and showing additional exemplary formulations that benefit from formulation with the reducing agents.

TABLE 5

| Component | Liquid Detergent A (wt-%) | Liquid Detergent B (wt-%) | Liquid Detergent C (wt-%) |
|---|---|---|---|
| Sodium hydroxide (NaOH), 50% | 47.5 | 47.5 | 47.5 |
| Polymers (Acumer 1000, 48%, Acusol 448 and/or Belclene 200) | 3-5 | 3-5 | 3-5 |
| Sodium bisulfite solution, 38% | 5.7 | 5.7 | 5.7 |
| Water | Remainder | Remainder | Remainder |
| Total | 100 | 100 | 100 |

100 cycle testing for various exemplary formulations as shown in the ranges of Table 5 were completed and yielded improved water conditioning results while retaining the benefits from the reduced residual chlorine concentration.

Example 4

Additional formulations containing the reducing agent were evaluated for assessing the amounts of bisulfite reducing agent to be included in the detergent compositions. Solutions were prepared as shown in Table 6 to assess for presence of any sulfur odor. Any sulfur odor was determined to be unacceptable in the kitchen environment so anything above a "0" score is deemed unacceptable in this evaluation (with complete scale shown in Table 7).

TABLE 6

| Description | Liquid Detergent Composition | +2% | +5% | +15% | +25% | Sodium Bisulfite |
|---|---|---|---|---|---|---|
| Water | 48.83 | 46.83 | 43.83 | 33.83 | 23.83 | |
| Phosphonobutane-tricarboxylic Acid, 50% | 2 | 2 | 2 | 2 | 2 | |
| Polyacrylic Acid, 48% | 1.60 | 1.60 | 1.60 | 1.60 | 1.60 | |
| NaOH, 50% | 47.57 | 47.57 | 47.57 | 47.57 | 47.57 | |
| Sodium Bisulfite Solution, 38% | | 2 | 5 | 15 | 25 | 100 |
| Sulfur Odor 1-4 | 0 | 0 | 0 | 1 | 2 | 4 |

TABLE 7

| Odor rankings: | |
|---|---|
| No sulfur odor | 0 |
| Faint sulfur odor | 1 |
| Moderate sulfur odor | 2 |
| Strong sulfur odor | 3 |
| Intense sulfur odor | 4 |

In embodiments the detergent compositions having the bisulfite reducing agents (whether in liquid or solid form) do not include the bisulfite in an amount that results in an odor.

In embodiments the bisulfite is less than about 15 wt-% (<5.7% active based on the material in the Example), or in some embodiments less than about 10 wt-%. It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims.

In addition, the contents of all patent publications discussed supra are incorporated in their entirety by this reference.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A method of reducing the rate of corrosion in a ware washing machine, comprising:

applying a sanitizing composition to ware in the ware washing machine to provide a sanitizing step, wherein the sanitizing composition comprises at least 30 ppm of chlorine;

reusing water from the sanitizing step to apply a use solution of a liquid or solid detergent composition free of enzymes and bleaching agents, and/or a booster composition to ware in a new wash cycle of the ware washing machine, wherein at least one of the liquid or solid detergent or the booster composition comprises a reducing agent that is a salt containing ammonium cation, and wherein the liquid detergent comprises from about 30 wt-% to about 70 wt-% of an alkalinity source or the solid detergent comprises from about 40 wt-% to about 90 wt-% of an alkalinity source;

reducing a residual chlorine concentration in the reused water for the detergent step of the warewash cycle to less than 20 ppm within 60 seconds; and reducing the rate of corrosion in the ware washing machine by at least about 50%.

2. The method of claim 1, wherein the residual chlorine concentration is reduced by at least about 50% or more.

3. The method of claim 1, wherein the use solution of the detergent composition and/or the booster composition comprises from about 10 ppm to about 100 ppm of the reducing agent.

4. A method of cleaning using a detergent composition that reduces the rate of corrosion in a ware washing machine, comprising:

applying to ware in the ware washing machine a use solution of the detergent composition free of enzymes and bleaching agents using water from a prior sanitizing rinse step containing at least 30 ppm of chlorine, the detergent composition comprising:

a reducing agent that is a salt containing ammonium cation;

about 30 wt-% to about 70 wt-% of an alkalinity source in a liquid detergent composition or about 40 wt-% to about 90 wt-% of an alkalinity source in a solid detergent composition, and;

at least one additional functional ingredient comprising at least one builder, at least one water conditioning polymer, and/or at least one surfactant;

reducing residual chlorine in the ware washing cycle during the detergent step to less than 20 ppm within 60 seconds and thereby reducing the rate of corrosion in the ware washing machine by at least about 50%; and thereafter;

applying a sanitizing composition to ware in the ware washing machine during the sanitizing step of the ware washing cycle, wherein the sanitizing composition comprises chlorine.

5. The method of claim 4, wherein the use solution of the detergent composition is diluted with water reused from the chlorine-containing sanitizing rinse step.

6. The method of claim 4, wherein the water used to generate the use solution of the detergent composition and/or rinsing ware with the sanitizing composition are heated to a temperature of at least about 120° F.

7. The method of claim 4, wherein the use solution of the detergent composition comprises from about 10 ppm to about 100 ppm of the reducing agent.

8. The method of claim 4, wherein the use solution of the detergent composition comprises a sufficient concentration of the reducing agent to reduce at least half of the residual chlorine in the use solution.

* * * * *